United States Patent
Lee et al.

(10) Patent No.: US 12,033,841 B2
(45) Date of Patent: Jul. 9, 2024

(54) METHOD FOR MEASURING ORGANIC MATTER IN BLOOD BY USING LDI-MS, AND DEVICE THEREFOR

(71) Applicant: KOREA RESEARCH INSTITUTE OF STANDARDS AND SCIENCE, Daejeon (KR)

(72) Inventors: Tae Geol Lee, Daejeon (KR); Hee-Kyung Na, Daejeon (KR); Sunho Joh, Daejeon (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 373 days.

(21) Appl. No.: 17/426,573

(22) PCT Filed: Dec. 30, 2019

(86) PCT No.: PCT/KR2019/018683
§ 371 (c)(1),
(2) Date: Jul. 28, 2021

(87) PCT Pub. No.: WO2020/159088
PCT Pub. Date: Aug. 6, 2020

(65) Prior Publication Data
US 2022/0084804 A1    Mar. 17, 2022

(30) Foreign Application Priority Data

Jan. 29, 2019  (KR) .................. 10-2019-0011493
Aug. 13, 2019  (KR) .................. 10-2019-0098646

(51) Int. Cl.
*H01J 49/04*    (2006.01)
*G01N 33/94*    (2006.01)
*H01J 49/00*    (2006.01)

(52) U.S. Cl.
CPC ...... *H01J 49/0418* (2013.01); *G01N 33/9493* (2013.01); *H01J 49/0031* (2013.01)

(58) Field of Classification Search
CPC .............. H01J 49/0418; H01J 49/0031; H01J 49/0036; H01J 49/164; G01N 33/9493; G01N 33/49; G01N 2560/00
See application file for complete search history.

(56) References Cited

U.S. PATENT DOCUMENTS

| 7,391,018 B2 * | 6/2008 | Niu ....................... A61L 27/303<br>428/650 |
| 7,567,596 B2 * | 7/2009 | Dantus ............... G01B 9/02091<br>372/27 |

(Continued)

FOREIGN PATENT DOCUMENTS

| CN | 103592361 A | 2/2014 |
| JP | 2005-083784 A | 3/2005 |

(Continued)

OTHER PUBLICATIONS

Kim et al., "A layer-by-layer assembled MoS2 thin film as an efficient platform for laser desorption/ionization mass spectrometry analysis of small molecules", Nanoscale, vol. 9, No. 30—19 pages (2017).

(Continued)

*Primary Examiner* — David A Vanore
(74) *Attorney, Agent, or Firm* — Knobbe Martens Olson & Bear LLP

(57) ABSTRACT

A method for detecting organic matter in the blood by using LDI-MS, and a device therefor, according to the present invention, are not complicated when performing measurement and do not require the passage of many steps, and facilitate, in real time, measurement and result collection through rapid analysis. In addition, the present invention enables precise analysis even at a lower sample concentra- (Continued)

tion so as to have excellent sensitivity and accuracy, enables the detection of various types of organic matter at the same time and has high throughput, and enables the structure analysis of organic matter, having undergone metabolic processes in the blood, and quantitative analysis thereof to be accurately performed without interference from a matrix.

18 Claims, 9 Drawing Sheets

(56) References Cited

U.S. PATENT DOCUMENTS 10,822,634 B2 * 11/2020 Northen ............. G01N 33/6848
11,264,221 B2 *  3/2022 Corkum ................ H01J 49/025

FOREIGN PATENT DOCUMENTS

| KR | 10-1592517 B1 | 2/2016 | |
|---|---|---|---|
| KR | 10-2018-0068280 A | 6/2018 | |
| WO | WO-2005016530 A1 * | 2/2005 | ............ B01L 3/5085 |

OTHER PUBLICATIONS

International Search Report of PCT Application No. PCT/KR2019/018683—4 pages (dated Apr. 10, 2020).
Office Action dated Sep. 25, 2023 in Korean Application No. 10-2019-0011493.

* cited by examiner

METHOD FOR MEASURING ORGANIC MATTER IN BLOOD BY USING LDI-MS, AND DEVICE THEREFOR

TECHNICAL FIELD

The present invention relates to a method for detecting an organic matter in blood and a device for detecting an organic matter in blood.

BACKGROUND ART

Therapeutic drug monitoring (TDM) measures concentrations of drugs and their metabolites in blood of patients at specified time intervals. Dosage of drugs for each individual may be adjusted through the therapeutic drug monitoring, and therapeutic effects for each individual through drugs may thus be maximized. The therapeutic drug monitoring with characteristics that include a relationship between a blood concentration and the therapeutic effect is very important.

There are various types of drugs such as immunosuppressive drugs, for example, a cardiac active drug. Pharmacokinetics and an inter-individual variation in a narrow therapeutic window may be monitored through the therapeutic drug monitoring.

The immunosuppressive drugs may be prescribed by doctors in order to induce suppression of an immune system for prevention of organ rejection in patients after organ transplantation. It is important to administer the drugs at an appropriate concentration in a treatment window in order to prevent side effects while generating an effect of the drugs. Due to their narrow therapeutic windows, the immunosuppressive drugs need to be infused at a correct concentration, and specifically, the drugs need to be measured in the blood of patients once or twice prior to infusion. In addition, the immunosuppressive drugs require the therapeutic drug monitoring due to an inter-individual difference in drug metabolism and pharmacokinetics. A conventional method most generally used in order to detect drugs in the blood of the patients is liquid chromatography-mass spectrometry (LC-MS). However, the LC-MS requires a number of experimental steps, is complicated, and requires much time, such that it is difficult to perform measurement in real time and it is not easy to collect measurement data immediately. Therefore, results of the immunosuppressive drugs in clinical samples need to be collected rapidly, and research into the therapeutic drug monitoring that enables direct and high-throughput detection as well as improvement of accuracy and sensitivity is required.

RELATED ART DOCUMENT

[Patent Document]
KR 10-2018-0068280A (Jun. 21, 2018)

DISCLOSURE

Technical Problem

An object of the present invention is to provide a method for detecting an organic matter in blood using LDI-MS that has a measurement process that is not complicated and does not require many measurement steps, and easily performs measurement and result collection through rapid analysis, and a device therefor.

Another object of the present invention is to provide a method for detecting an organic matter in the blood using LDI-MS that may perform precise analysis even at a lower sample concentration to be excellent in terms of sensitivity and accuracy, may detect various types of organic matters, has a high throughput, and may accurately perform structure analysis of an organic matter subjected to a metabolic process in the blood, and quantitative analysis thereof to be accurately performed without interference with a matrix, and a device therefor.

Technical Solution

In one general aspect, a method for detecting an organic matter using LDI-MS includes: a sample loading step of loading the sample containing blood on a tungsten disulfide layer of an LDI-MS sample loading array including a substrate layer, and the tungsten disulfide layer stacked on the substrate layer; and an analyzing step of analyzing the sample mounted on the LDI-MS sample loading array by LDI-MS to detect a target matter in the sample.

The analyzing step may include a quantifying step of calculating a content of the target matter.

The quantifying step may include a first quantifying step of obtaining a concentration of tungsten disulfide nanoflake particles present in the tungsten disulfide layer, and the content of the target matter may be determined from the concentration of the tungsten disulfide nanoflake particles obtained in the first quantifying step.

The method for analyzing a sample in blood using LDI-MS may further include, before the sample loading step, adding an internal standard to a liquid sample, wherein the quantifying step includes a second quantifying step of determining the content of the target matter from a peak intensity corresponding to the target matter and a peak intensity corresponding to the internal standard in LDI-MS spectrum.

The quantifying step may include obtaining a corrected spectrum, wherein a coefficient of determination in the corrected spectrum may be 0.9 or more.

In the method for analyzing a sample in blood using LDI-MS, a limit of detection (LoD) may be 0.01 pmol/$\mu$l (target matter/blood) or less.

In another general aspect, an LDI-MS sample loading array for detecting an organic matter in blood includes: a substrate layer; and a tungsten disulfide layer stacked on the substrate layer and allowing a sample containing blood to be loaded.

The tungsten disulfide layer may include a plurality of tungsten disulfide nanoflake particles in contact with the substrate layer.

The tungsten disulfide nanoflake particles may have an average thickness of 2 to 15 nm.

In the tungsten disulfide layer, the tungsten disulfide nanoflake particles may be present in an amount of 0.0001 to 100 mg/cm$^2$ per unit area.

The tungsten disulfide layer may be prepared by spotting an aqueous dispersion solution in which the tungsten disulfide nanoflake particles are dispersed, on the substrate layer, and then evaporating water.

The aqueous dispersion solution may contain 0.001 to 10% by weight of the tungsten disulfide nanoflake particles.

The aqueous dispersion solution may be spotted twice or more in the same area with a content of 0.001 to 100 $\mu$l (25° C. and 1 atm).

The tungsten disulfide layer may have an average thickness of 0.001 to 500 $\mu$m.

The tungsten disulfide nanoflake particles may satisfy Equation 1. In Equation 1, $R_1$ is a peak area in a range of 340 to 380 cm$^{-1}$ in a Raman spectrum measured in an arbitrarily selected region of 2×2 μm in the tungsten disulfide layer, and $R_2$ is a peak area in a range of 400 to 440 cm$^{-1}$ in the Raman spectrum.

$$R_1/R_2 \geq 1.3 \qquad \text{Equation 1:}$$

The tungsten disulfide nanoflake particles may be prepared by a lithium-intercalated chemical exfoliation method from tungsten disulfide (WS$_2$) bulk powders.

The substrate layer may include any one or two or more selected from aluminum, copper, iron, nickel, zinc, chromium, silver, and silicone (SiO$_2$).

The sample loading array may be used for qualitative or quantitative analysis of a target matter injected into blood.

In another general aspect, there is provided a sample loading kit for LDI-MS including the LDI-MS sample loading array for detecting organic matter in the blood as described above.

In another general aspect, there is provided a laser desorption ionization mass spectrometry device including: the LDI-MS sample loading array for detecting organic matter in the blood as described above.

Advantageous Effects

A method for detecting organic matter in the blood by using LDI-MS, and a device therefor, according to the present invention, are not complicated when performing measurement and do not require the passage of many steps, and facilitate, in real time, measurement and result collection through rapid analysis.

A method for detecting organic matter in the blood by using LDI-MS, and a device therefor, according to the present invention enables precise analysis even at a lower sample concentration so as to have excellent sensitivity and accuracy, enables the detection of various types of organic matter at the same time and has high throughput, and enables the structure analysis of organic matter, having undergone metabolic processes in the blood, and quantitative analysis thereof to be accurately performed without interference from a matrix.

Even if the effect is not explicitly mentioned in the present invention, the effects described in the specification expected by technical features of the present invention and the inherent effects thereof, are treated as described in the specification of the present invention.

BEST MODE

Figure 1:
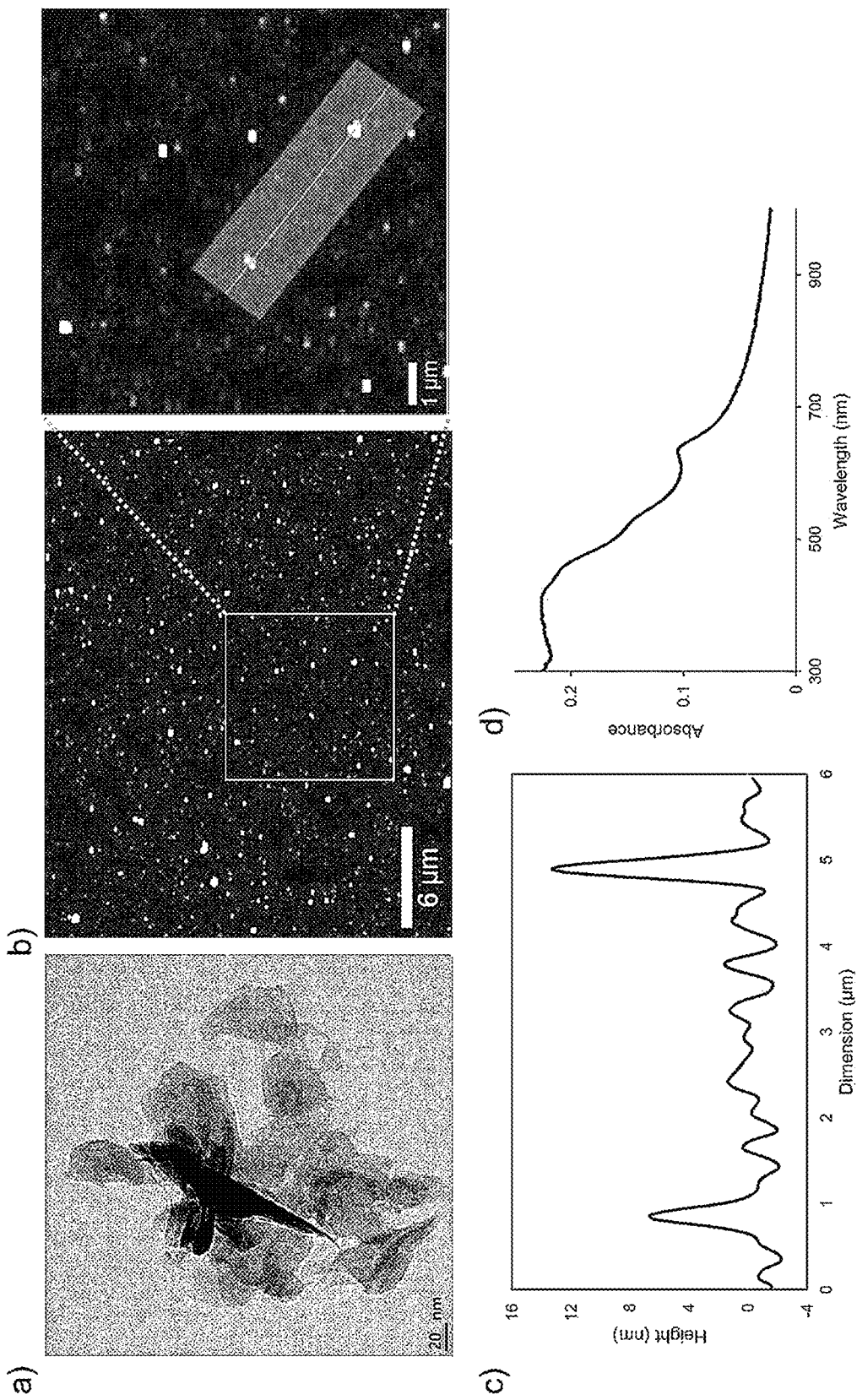
FIG. 1 shows (a) a transmission electron microscope (TEM) image of tungsten disulfide nanoflake particles, (b) and (c) atomic force microscope (AFM) images of tungsten disulfide nanoflake particles, and (d) a UV-Vis spectrum of tungsten disulfide nanoflake particles.

Hereinafter, a method for detecting organic matter in blood using LDI-MS and a device therefor, according to the present invention, will be described in detail with reference to the accompanying drawings.

The drawings described in this specification are provided as examples so that the spirit of the present invention can be sufficiently transferred to those skilled in the art. Therefore, the present invention is not limited to the accompanying drawings provided and may be embodied in other forms. In addition, the accompanying drawings suggested below will be exaggerated in order to clarify the spirit of the present invention.

As used herein, technical terms and scientific terms have the general meaning understood by those skilled in the art to which the present invention pertains unless otherwise defined, and a description for the known function and configuration unnecessarily obscuring the gist of the present invention will be omitted in the following description and the accompanying drawings.

As used herein, the singular form of terms may be interpreted as including the plural form unless otherwise indicated.

As used herein, the term itself referring to each step, such as s1, s2, s3, . . . ; a1, a2, a3, . . . ; b1, b2, b3, . . . ; and a, b, c, . . . , is only used to refer to certain steps, means, etc., and should not be construed as implying an ordered relationship of the respective objects to which the terms refer.

The unit of % used herein refers to % by weight unless otherwise specified.

As used herein, the term "layer" or "film" means that each material forms a continuum and has a relatively small dimension in thickness versus width and length.

Accordingly, as used herein, the term "layer" or "film" should not be interpreted as a two-dimensional flat plane.

The present invention provides a method for detecting organic matter in the blood using LDI-MS, an LDI-MS sample loading array for detecting organic matter in the blood, a sample loading kit for LDI-MS including the array, and a laser desorption ionization mass spectrometry device including the array. As used herein, LDI-MS refers to a laser desorption/ionization mass spectrometry (LDI-MS).

In the present invention, as a chip-based LDI-MS array may be manufactured using uniformly deposited tungsten disulfide ($WS_2$) nanoflake particles, a simple platform for high-throughput analysis may be provided, and partial or complete automation of sample preparation is possible, thereby significantly reducing analysis time. In addition, accuracy and precision in mass spectrometry may be significantly improved. Therefore, unlike the case of LC-MS/MS in which the steps are complicated and real-time detection is practically difficult, the present invention has the effect that the real-time detection and analysis of the organic matter is possible and the precision of qualitative and quantitative analysis is more excellent.

A method for detecting organic matter in the blood using LDI-MS according to the present disclosure includes: a sample loading step for loading the sample containing blood on a tungsten disulfide layer of an LDI-MS sample loading array including a substrate layer, and the tungsten disulfide layer stacked on the substrate layer; and an analysis step of analyzing the sample mounted on the LDI-MS sample loading array by LDI-MS to detect a target matter in the sample.

As tungsten disulfide is applied to a surface layer of an LDI-MS sample plate in the form of nanoparticles, the method according to the present invention has high precision in qualitative and quantitative analysis of organic matter in the blood, and in particular, has high accuracy in quantitative analysis, which has the effect of accurately measuring the content of an organic matter to be analyzed, that is, a target molecule. Thus, the method according to the present invention has the effect of being able to qualitatively and quantitatively analyze organic matter in the blood in real time because qualitative and quantitative analysis with high precision and accuracy are possible, while the analysis method is simple and the time required is very short. These effects are because tungsten disulfide is used as nanoparticles in the surface layer of the LDI-MS sample plate, and it is difficult to implement when a metal compound other than tungsten disulfide is used, for example, when another metal compound such as molybdenum disulfide ($MoS_2$) or tungsten dioxide ($WO_2$) is used.

In an embodiment of the present invention, the analyzing step may include a quantifying step of calculating the content of the target matter. Specifically, the first quantifying step of analyzing the content of the target matter from the concentration of the tungsten disulfide nanoflake particles, or the second quantifying step through an internal standard may be exemplified.

As a specific example, the first quantifying step will be described. The quantifying step may include a first quantifying step of obtaining the concentration of tungsten disulfide nanoflake particles present in the tungsten disulfide layer, and the content of the target matter may be determined from the concentration of the tungsten disulfide nanoflake particles obtained in the first quantifying step.

As a specific example, the second quantifying step will be described. The sample analysis method using LDI-MS according to an example of the present invention may include, before the sample loading step, adding an internal standard to a liquid sample, wherein the quantifying step may include a second quantifying step of determining the content of the target matter from a peak intensity corresponding to the target matter and a peak intensity corresponding to the internal standard in LDI-MS spectrum. The internal standard may be any matter as long as it is distinguishable from the target matter in the analysis step and physicochemical properties (ionization properties and solubility) are similar to those of the target matter. Precise quantitative analysis of the target matter is possible due to a difference in molecular weight using this internal standard.

In an embodiment of the present invention, the quantifying step may include obtaining a calibration spectrum, and a coefficient of determination in the calibration spectrum may be 0.9 or more, specifically 0.93 or more, and more specifically 0.95 or more. That is, the present invention is significantly excellent in the precision of quantitative analysis. In this case, an upper limit of 1 or less is enough.

In the sample analysis method using LDI-MS according to an embodiment of the present invention, a limit of detection (LoD) may be 0.01 pmol/μL (target matter/blood) or less. That is, the present invention has the effect of enabling precise quantitative analysis even when a very small amount of blood is used.

An LDI-MS sample loading array for detecting organic matter in the blood, according to the present invention includes a substrate layer; and a tungsten disulfide layer stacked on the substrate layer and allowing a sample containing blood to be loaded.

In an embodiment of the present invention, the tungsten disulfide layer may include a plurality of tungsten disulfide nanoflake particles in contact with the substrate layer.

At least one of a short width, a long width, and a thickness of the tungsten disulfide nanoflake has a nano size, and the tungsten disulfide nanoflake has a plate shape. The tungsten disulfide nanoflakes may be prepared by various methods, and for example, a chemical exfoliation method, specifically, a lithium-intercalated chemical exfoliation method from tungsten disulfide ($WS_2$) bulk powders may be a manufacturing means, but any other means capable of preparing a nano-sized plate-shaped tungsten disulfide may be used.

The following examples may be given when the specifications of the tungsten disulfide nanoflake particles are specifically described in their specifications, but this is only described as a preferred example, and the present invention is not necessarily construed as being limited thereto. As a preferred example, the tungsten disulfide nanoflake particles may have an average thickness of 1 to 50 nm, specifically 2 to 15 nm, and an average long width of 1 to 5,000 nm, and may be present on the substrate layer in an amount of 0.0001 to 100 mg/cm² per unit area. In addition, the tungsten disulfide layer may have a surface roughness of 1 to 500 nm.

The tungsten disulfide layer may be prepared by spotting a dispersion solution in which tungsten disulfide nanoflake particles are dispersed on the substrate layer, and then evaporating the dispersion solution. In this case, the dispersion solution may include any one or more dispersion media selected from water and a known organic solvent, etc., and the dispersion medium may be preferably water, and more preferably an aqueous dispersion solution. When forming a tungsten disulfide layer containing the tungsten disulfide nanoflake particles on the substrate layer by spotting and drying the dispersion solution, there are effects that a dispersed loading state of a regular pattern may be maintained in a more stable structure, and more precise qualitative analysis and quantitative analysis are possible.

A composition ratio of the dispersion solution is not particularly limited because it may be adjusted so that the tungsten disulfide nanoflake particles are finally dispersed on the substrate layer to exist in a loaded state in an appropriate amount. However, for example, the dispersion solution may contain 0.001 to 10% by weight of the tungsten disulfide nanoflake particles and the remaining amount of the dispersion medium.

In an embodiment of the present invention, spotting the dispersion solution 2 or more times, and specifically 2 to 10 times in the same area with an amount of 0.001 to 100 μl (25° C., 1 atm), may maintain a distributed loading state of a regular pattern in a more stable structure, and may perform more precise qualitative and quantitative analysis.

The average thickness of the tungsten disulfide layer may be appropriately controlled according to the loading amount and a loading state of the tungsten disulfide nanoflake particles, and may be, for example, 0.001 to 500 μm. If the thickness is within the above range, a more stably loaded state may be maintained, and more precise qualitative and quantitative analysis are possible. In addition, a width (breadth or length) of the tungsten disulfide layer is not particularly limited because it may be appropriately adjusted according to an analysis/measurement scale, and may be, for example, 0.001 to 10 mm.

In an embodiment of the present invention, the tungsten disulfide nanoflake particles may satisfy Equation 1. In Equation 1, $R_1$ is a peak area in the range of 340 to 380 cm$^{-1}$ in the Raman spectrum and $R_2$ is a peak area in the range of 400 to 440 cm$^{-1}$ in the Raman spectrum, as measured in an arbitrarily selected region of 2×2 μm in the tungsten disulfide layer $$R_1/R_2 \geq 1.3 \qquad \text{Equation 1:}$$

The substrate layer may be various, and for example, may include any one or two or more selected from a conductive metal such as aluminum, copper, iron, nickel, zinc, chromium, and silver, and silicone (SiO$_2$), etc. However, the above-mentioned examples are only described as specific examples, and the present invention is not necessarily construed as being limited thereto.

As described above, a method for detecting organic matter using LDI-MS according to the present invention and a device therefor may be used for qualitative or quantitative analysis of a target matter in the blood or a target matter injected into the blood.

As used herein, a "sample" means blood or those containing the blood. As the blood, blood itself may be used, plasma separated from blood may be used, and any treated blood may be used.

As used herein, "organic matter" for detection may mean "target matter", and the target matter may preferably be a target molecule. The target matter is not limited as long as it is organic matter to be detected in the blood, and may include, for example, various agents such as an immunosuppressive drug, an anti-migration agent, an anti-inflammatory agent, an angiogenesis inhibitor, a cytostatic agent, a cytotoxic agent, an anti-restenotic agent, an anti-malignant tumor agent, an antibacterial agent, and an antifungal agent. In addition, the target matter may be used for injection into the blood requiring monitoring.

As a non-limiting and specific example, the target matter may include various components, for example, cyclosporin A, tacrolimus, sirolimus, everolimus, abciximab, acemethacin, acetylbismion B, aclarubicin, ademethionine, adriamycin, aescin, apromoson, akagerin, aldesleukin, amidorone, aminoglutethimide, amsacrine, anakinra, anastrozole, anemonin, aminopterin, antifungal agents, antithrombotic agents, aposimarin, argatroban, aristolactam-AII, aristolochic acid, ascomycin, asparaginase, aspirin, atorvastatin, auranofin, azathioprine, azithromycin, baccatin, bafilomycin, basiliximab, bendamustine, benzocaine, berberine, betulin, betulinic acid, bilobol, bisparthenolidine, bleomycin, bombrestatin, boswellic acids and derivatives thereof, bruceanoles A, B and C, bryophyllin A, busulfan, antithrombin, bivalirudin, cadherins, camptothecin, capecitabine, o-carbamoyl-phenoxy-acetic acid, carboplatin, carmustine, celecoxib, cepharanthin, cerivastatin, CETP inhibitors, chlorambucil, chloroquine phosphate, cictoxin, ciprofloxacin, cisplatin, cladribine, clarithromycin, colchicine, concanamycin, coumadin, C-type Natriuretic peptide (CNP), cudraisoflavone A, curcumin, cyclophosphamide, cyclosporine A, cytarabine, dacarbazine, daclizumab, dactinomycin, dapson, daunorubicin, diclofenac, 1,11-dimethoxycanthin-6-one, docetaxel, doxorubicin, daunomycin, epirubicin, epothilones A and B, erythromycin, estramustine, etoposide, filgrastim, fluoroblastin, fluvastatin, fludarabine, fludarabine-5'-dihydrogenphosphate, fluorouracil, folimycin, fosfestrol, gemcitabine, ghalakinoside, ginkgol, ginkgolic acid, glycoside 1a, 4-hydroxyoxycyclophosphamide, idarubicin, ifosfamide, josamycin, lapachol, lomustine, lovastatin, melphalan, midecamycin, mitoxantrone, nimustine, pitavastatin, pravastatin, procarbazin, mitomycin, methotrexate, mercaptopurine, thioguanine, oxaliplatin, irinotecan, topotecan, hydroxycarbamide, miltefosine, pentostatin, pegaspargase, exemestane, letrozole, formestane, mitoxantrone, mycophenolate mofetil, β-lapachone, podophyllotoxin, podophyllic acid 2-ethylhydrazide, molgramostim (rhuGM-CSF), peginterferon α-2b, lenograstim (r-HuG-CSF), macrogol, selectin (cytokine antagonist), cytokinin inhibitors, COX-2 inhibitor, angiopeptin, monoclonal antibodies that inhibit muscle cell proliferation, bFGF antagonists, probucol, prostaglandins, 1-hydroxy-11-methoxycanthin-6-one, scopoletin, NO donors, pentaerythritol tetranitrate and sydnonimines, S-nitroso derivatives, tamoxifen, staurosporine, β-estradiol, α-estradiol, estriol, estrone, ethinylestradiol, medroxyprogesterone, estradiol cypionates, estradiol benzoates, tranilast, kamebakaurin and other terpenoids used in cancer therapy, verapamil, tyrosine kinase inhibitors (tyrphostins), paclitaxel and derivatives thereof, 6-α-hydroxy-paclitaxel, taxotere, mofebutazone, lonazolac, lidocaine, ketoprofen, mefenamic acid, piroxicam, meloxicam, penicillamine, hydroxychloroquine, sodium aurothiomalate, oxaceprol, β-sitosterin, myrtecaine, polidocanol, nonivamide, levomenthol, ellipticine, D-24851 (Calbiochem), colcemid, cytochalasin A-E, indanocine, nocadazole, bacitracin, vitronectin receptor antagonists, azelastine, guanidyl cyclase stimulator tissue inhibitor of metal proteinase-1 and -2, free nucleic acids, nucleic acids incorporated into virus transmitters, DNA and RNA fragments, plasminogen activator inhibitor-1, plasminogen activator inhibitor-2, antisense oligonucleotides, VEGF inhibitors, IGF-1, active agents from the group of antibiotics, cefadroxil, cefazolin, cefaclor, cefoxitin, tobramycin, gentamycin, penicillins, dicloxacillin, oxacillin, sulfonamides, metronidazole, enoxaparin, heparin, hirudin, PPACK, protamine, prourokinase, streptokinase, warfarin, urokinase, vasodilators, dipyridamol, trapidil, nitroprussides, PDGF antagonists, triazolopyrimidine, seramin, ACE inhibitors, captopril, cilazapril, lisinopril, enalapril, losartan, thioprotease inhibitors, prostacyclin, vapiprost, interferon α, β and γ, histamine antagonists, serotonin blockers, apoptosis inhibitors, apoptosis regulators, halofuginone, nifedipine, paracetamol, dexpanthenol, clopidogrel, acetylsalicylic acid derivatives, streptomycin, neomycin, framycetin, paromomycin, ribostamycin, kanamycin, amikacin, arbekacin, bekanamycin, dibekacin, spectinomycin, hygromycin b, paromomycinsulfate, netilmicin, sisomicin, isepamicin, verdamicin, astromicin, apramycin, geneticin, amoxicillin, ampicillin, bacampicillin, pivmecillinam, flucloxacillin, mezlocillin, piperacillin, azlocillin, temocillin, ticarcillin, amoxicillin, clavulanic acid, ampicillin, sulbactam, piperacillin, tazobactam, sulbactam, cefamandol, cefotiam, cefuroxim, cefmenoxim, cefodizim, cefoperazon, cefotaxim, ceftazidim, cefsulodin, ceftriaxon, cefepim, cefpirom, cefoxitin, cefotetan, cefalexin, cefuroxim axetil, cefixim, cefpodoxim, ceftibuten, imipenem, meropenem, ertapenem, doripenem, aztreonam, spiramycin, azithromycin, telithromycin, quinopristin, dalfopristin, clindamycin, tetracycline, doxycyclin, minocyclin, trimethoprim, sulfamethoxazol, sulfametrol, nitrofurantoin, lomefloxacin, norfloxacin, ciprofloxacin, ofloxacin, fleroxacin, levofloxacin, sparfloxacin, moxifloxacin, vancomycin, teicoplanin, linezolid, daptomycin, rifampicin, fusidic acid, fosfomycin, trometamol, chloramphenicol, metronidazol, colistin, mupirocin, bacitracin, neomycin, fluconazol, itraconazol, voriconazol, posaconazol, amphotericin b, 5-flucytosin, caspofungin, anidulafungin, tocopherol, tranilast, molsidomine, tea polyphenols, epicatechin gallate, epigallocatechin gallate, leflunomide, etanercept, sulfasalazine, etoposide, dicloxacillin, tetracycline, triamcinolone, mutamycin, procainimide, retinoic acid, quinidine, disopyramide, flecamide, propafenone, sotolol, naturally and synthetically obtained steroids, inotodiol, maquiroside A, ghalakinoside, mansonine, strebloside, hydrocortisone, betamethasone, dexamethasone, non-steroidal substances (NSAIDS), fenoprofen, ibuprofen, indomethacin, naproxen, phenylbutazone, acyclovir, ganciclovir, zidovudin, clotrimazole, flucytosine, griseofulvin, ketoconazole, miconazole, nystatin, terbinafine, antiprotozoal agents, chloroquine, mefloquine, quinine, natural terpenoids, hippocaesculin, barringtogenol-C21-angelat, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceantinoside C, yadanziosides N and P, isodeoxyelephantopin, tomenphantopin A and B, Coronarin A, B, C and D, ursolic acid, hyptatic acid A, iso-iridogermanal, maytenfoliol, effusantin A, excisanin A and B, longikaurin B, sculponeatin C, kamebaunin, leukamenin A and B, 13,18-dehydro-6-alpha-senecioyloxychaparrin, taxamairin A and B, regenilol, triptolide, cymarin, hydroxyanopterin, protoanemonin, cheliburin chloride, sinococuline A and B, dihydronitidine, nitidine chloride, 12-beta-hydroxypregnadien-3,20-dion, helenalin, indicine, indicine-N-oxide, lasiocarpine, inotodiol, podophyllotoxin, justicidin A and B, larreatin, malloterin, mallotochromanol, isobutyrylmallotochromanol, maquiroside A, marchantin A, maytansine, lycoridicin, margetine, pancratistatin, liriodenine, bisparthenolidine, oxoushinsunine, periplocoside A, ursolic acid, deoxypsorospermin, psycorubin, ricin A, sanguinarine, manwu wheat acid, methylsorbifolin, sphatheliachromen, stizophyllin, mansonine, strebloside, dihydrousambaraensine, hydroxyusambarine, strychnopentamine, strychnophylline, usambarine, usambarensine, liriodenine, oxoushinsunine, daphnoretin, lariciresinol, methoxylariciresinol, syringaresinol, biolimus A9, myolimus, novolimus, pimecrolimus, ridaforolimus, deoxorapamycin, temsirolimus and zotarolimus, somatostatin, tacrolimus, roxithromycin, troleandomycin, simvastatin, rosuvastatin, vinblastine, vincristine, vindesine, teniposide, vinorelbine, trofosfamide, treosulfan, temozolomide, thiotepa, tretinoin, spiramycin, umbelliferone, desacetylvismione A, vismione A and B, zeorin and sulfur-containing amino acids such as cystine as well as salts, hydrates, solvates, enantiomers, racemates, enantiomeric mixtures, and diastereomeric mixtures. However, the above-mentioned examples are only described as specific examples, and the present invention is not necessarily construed as being limited thereto.

The immunosuppressive drug is a drug that blocks or inhibits the activity of the immune system of a living body, may be a matter that may be used for immunosuppressive therapy, and may be a molecule that may be detected by a detection method or a measuring device according to the present invention. The immunosuppressive drug is not limited in its type, and may include any one or two or more selected from, for example, cyclosporine, tacrolimus, azathioprine, mycophenolic acid, sirolimus (rapamycin), everolimus, temsirolimus, deforolimus, rituximab, steroid, mycrophenolate mofetil, anti-CD3 antibody, cyclophosphamide, ifosfamide, and derivatives thereof, for better understanding. However, the above-mentioned examples are only described as specific examples, and the present invention is not necessarily construed as being limited thereto.

The analysis/measurement method and device according to the present invention may be applied in various forms in various fields. For example, the present invention may also be provided as a sample loading kit for LDI-MS including an LDI-MS sample loading array, and may also be provided as a laser desorption ionization mass spectrometry device including an LDI-MS sample loading array.

Hereinafter, the present invention will be described in detail through preparation examples and examples, but the examples are for the purpose of describing the present invention in more detail, and the scope of the present invention is not limited by the following examples.

Preparation Example 1

<Preparation of Tungsten Disulfide Nanoflake Particles>

Using a lithium-intercalated chemical exfoliation method from tungsten disulfide ($WS_2$) powders having an average particle diameter of 90 nm, tungsten disulfide nanoflake particles were synthesized as follows.

2.5 g of tungsten disulfide bulk powders were dispersed in 20 ml of hexane (molar ratio of 1:1) containing lithium chloride, and were subjected to ultrasonic treatment for 120 minutes to prepare a dispersion containing lithium-tungsten disulfide compound ($Li_xWS_2$). The dispersion was centrifuged at 4,000 rpm for 10 minutes to remove hexane and unreacted materials. The lithium-tungsten disulfide compound was dispersed in dimethylformamide (DMF), followed by centrifugation and washing to obtain a solvated lithium-tungsten disulfide compound (($Li$-solvent)$_xWS_2$). The solvated lithium-tungsten disulfide compound was subjected to mild ultrasonic treatment at room temperature to exfoliate the tungsten disulfide in 500 ml of dimethylformamide. Thus, intercalated lithium is solvated in the presence of a dispersion solvent and exfoliated by physical impact to prepare tungsten disulfide nanoflake particles.

Example 1

<Manufacture of LDI-MS Array>

For a reproducible and uniform analysis platform, a tungsten disulfide dispersion in which 5 g of powder containing tungsten disulfide nanoflake particles was dispersed in 50 g of water was prepared, using a micro-droplet distributor. Then, a chip-based LDI-MS array was prepared using the tungsten disulfide dispersion. Specifically, an LDI-MS array including a tungsten disulfide layer formed by spotting a tungsten disulfide dispersion on a stainless steel wafer having a thickness of 1 mm using a micro-droplet distributor, and sufficiently drying the tungsten disulfide dispersion to uniformly deposit tungsten disulfide nanoflake particles on the stainless steel wafer was prepared. In this case, the volume of the tungsten disulfide dispersion per spotting was adjusted to 0.1 µl.

[Experimental Example 1] Evaluation of Properties of Tungsten Disulfide Nanoflake Particles FIG. 1 shows (a) a transmission electron microscope (TEM) image of tungsten disulfide nanoflake particles, (b) and (c) atomic force microscope (AFM) images of tungsten disulfide nanoflake particles, and (d) a UV-Vis spectrum of tungsten disulfide nanoflake particles.

As illustrated in FIG. 1, tungsten disulfide nanoflake particles having a flake thickness in a range of about 2 to 14 nm were dispersed in water on a large scale to prepare a tungsten disulfide dispersion. The exfoliated tungsten disulfide nanoflake particles had a zeta potential value of 18.3 (±0.5) eV. A UV-Vis spectrum (Nd: YAG laser) of the tungsten disulfide dispersion showed strong absorption at a wavelength of 350 to 450 nm.

Figure 2:
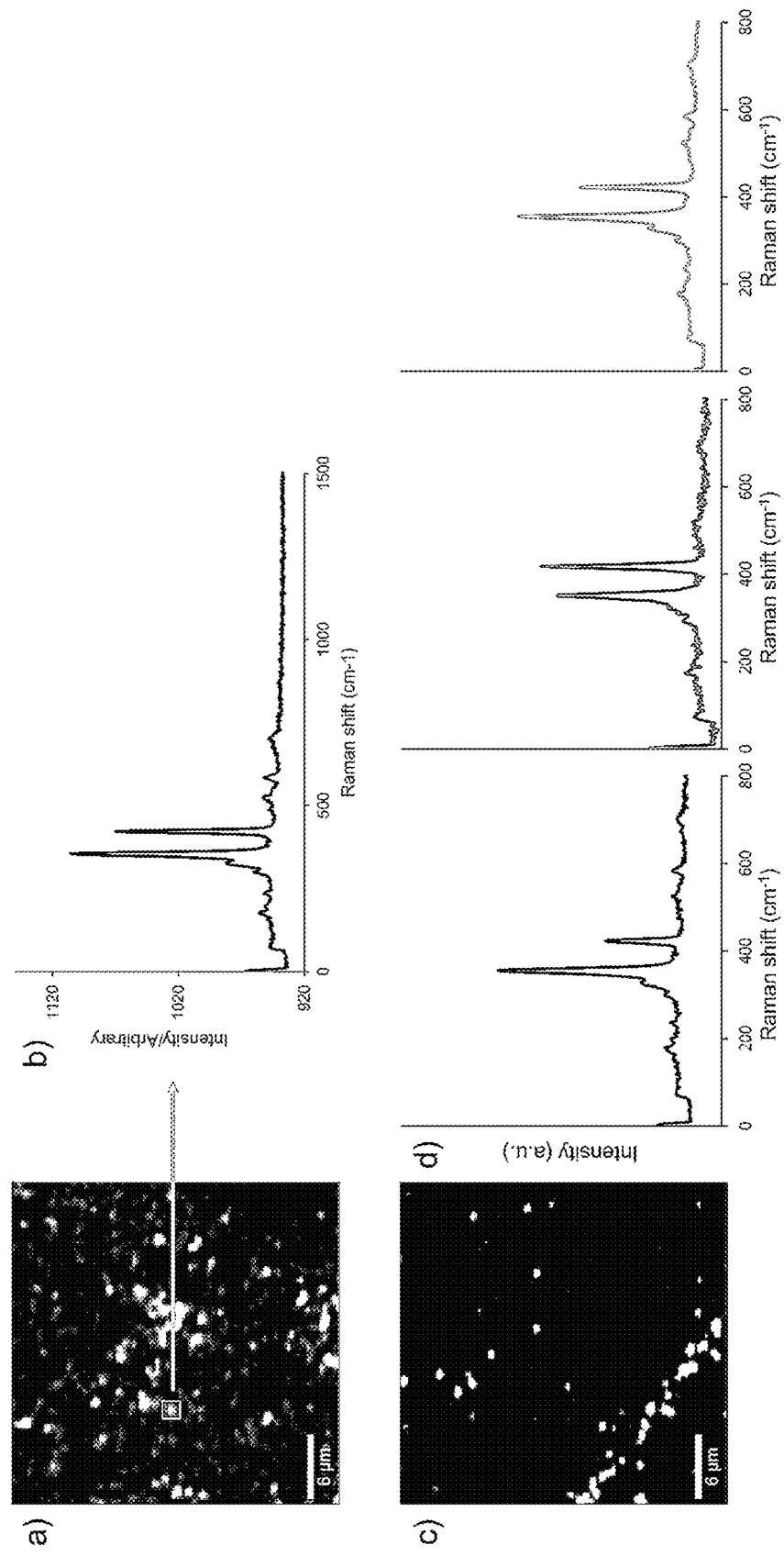
FIG. 2 shows (a) a Raman mapping result for a tungsten disulfide layer on a wafer, (b) a Raman spectrum extracted from a region (2×2 μm) selected in Raman mapping of (a) of FIG. 2, (c) a Raman mapping result with peaks at wavelengths of 350 cm$^{-1}$ (red) and 420 cm$^{-1}$ (green), and (d) a Raman spectrum extracted from a red region (left spectrum), a green region (center spectrum), and a yellow region (right spectrum) from Raman mapping.

FIG. 2 (a) a Raman mapping result for a tungsten disulfide layer on a wafer, (b) a Raman spectrum extracted from a region (2×2 µm) selected in Raman mapping of (a) of FIG. 2, (c) a Raman mapping result with peaks at wavelengths of 350 $cm^{-1}$ (red) and 420 $cm^{-1}$ (green), and (d) a Raman spectrum extracted from a red region (left spectrum), a green region (center spectrum), and a yellow region (right spectrum) from Raman mapping.

As illustrated in FIG. 2, it can be confirmed that several layered tungsten disulfide nanoflake particles are present by comparing intensities from the mapping with the peaks at 350 and 420 $cm^{-1}$ wavelengths corresponding to an $E^1_{2g}$ mode and an $A_{1g}$ mode.

Figure 3:
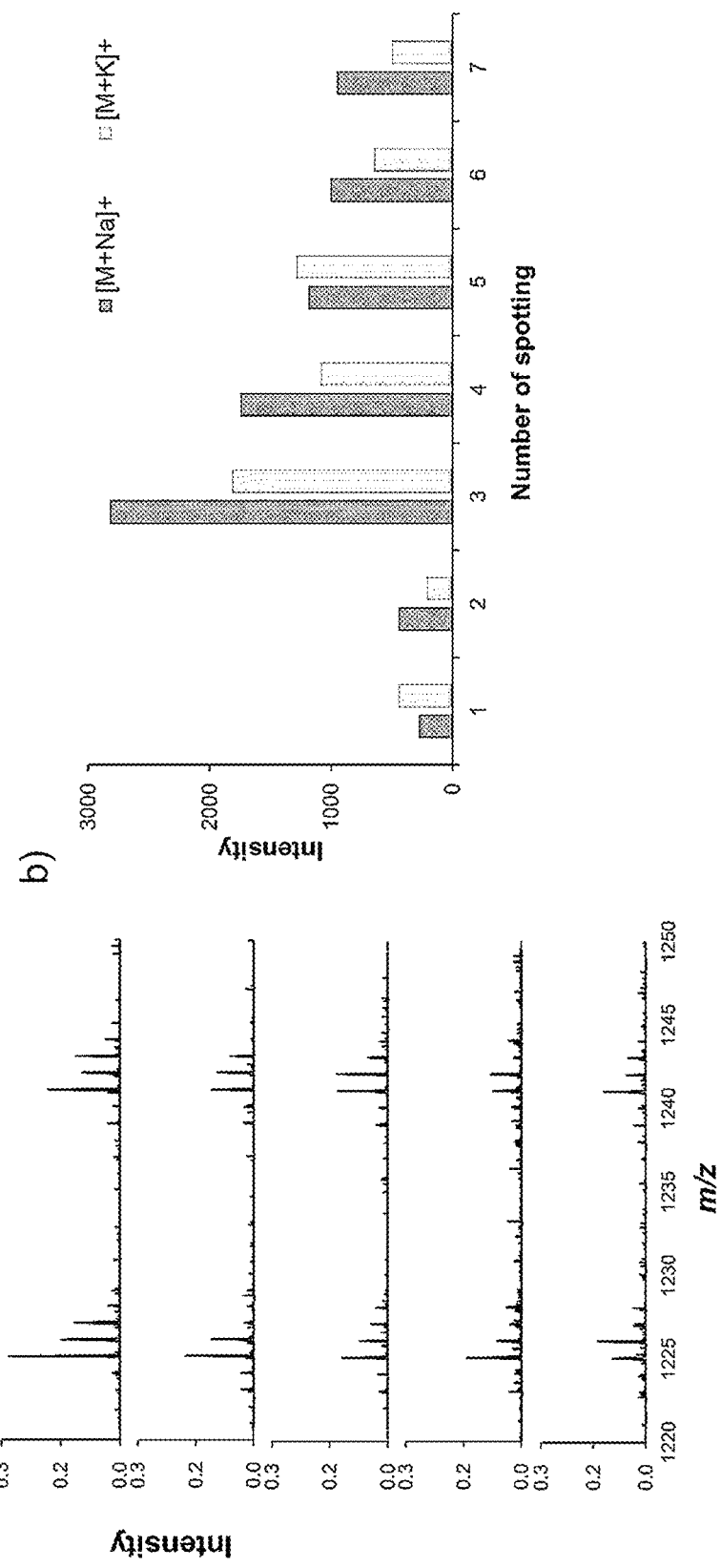
FIG. 3 shows (a) an intensity of CsA using LDI-MS analysis depending on the number of spotting of tungsten disulfide dispersion, and (b) a graph showing a relationship between the intensity of CsA and the number of spotting using LDI-MS analysis.

As such, it can be confirmed from FIGS. 1 to 3 that the tungsten disulfide nanoflake particles on the substrate form an array in a regular pattern after spotting.

[Experimental Example 2] Thickness Analysis of Tungsten Disulfide Layer

As illustrated in FIG. 3, an optimum thickness of the tungsten disulfide layer was confirmed by adjusting the number of spotting. In this case, the volume of the tungsten disulfide dispersion per spotting was adjusted to 0.1 µl, and the relationship between the number and mass signal intensity of layers was illustrated in FIG. 3. As illustrated in FIG. 3, the peak intensity was the strongest when spotting was performed three times, so a quantitative analysis of the four immunosuppressive drugs in the blood was performed using such a condition.

[Experimental Example 3] Quantitative Analysis Evaluation of Target Matter Using LDI-MS Array Since it is difficult to directly determine the concentration of a drug due to unpredictable ionization behavior of molecules, the addition of an internal standard with similar desorption/ionization properties is required. That is, in order to quantify the content of a target matter in a clinical sample, an internal standard having physicochemical properties (ionization properties and solubility, etc.) similar to the target molecule was used. Mass analysis of the target matter is possible due to a difference in molecular weight using the internal standard.

In order to monitor the concentration of the target matter in the blood of the patients during treatment after organ transplantation, sensitivity to tungsten disulfide nanoflake particles was confirmed as a matter for LDI-MS. Cyclosporine A (CsA), Tacrolimus (TAC), Sirolimus (SIR) and Everolimus (EVR), which are commonly used immunosuppressive drugs, were used as the target matter.

<Quantitative Analysis of CsA>

Figure 4:
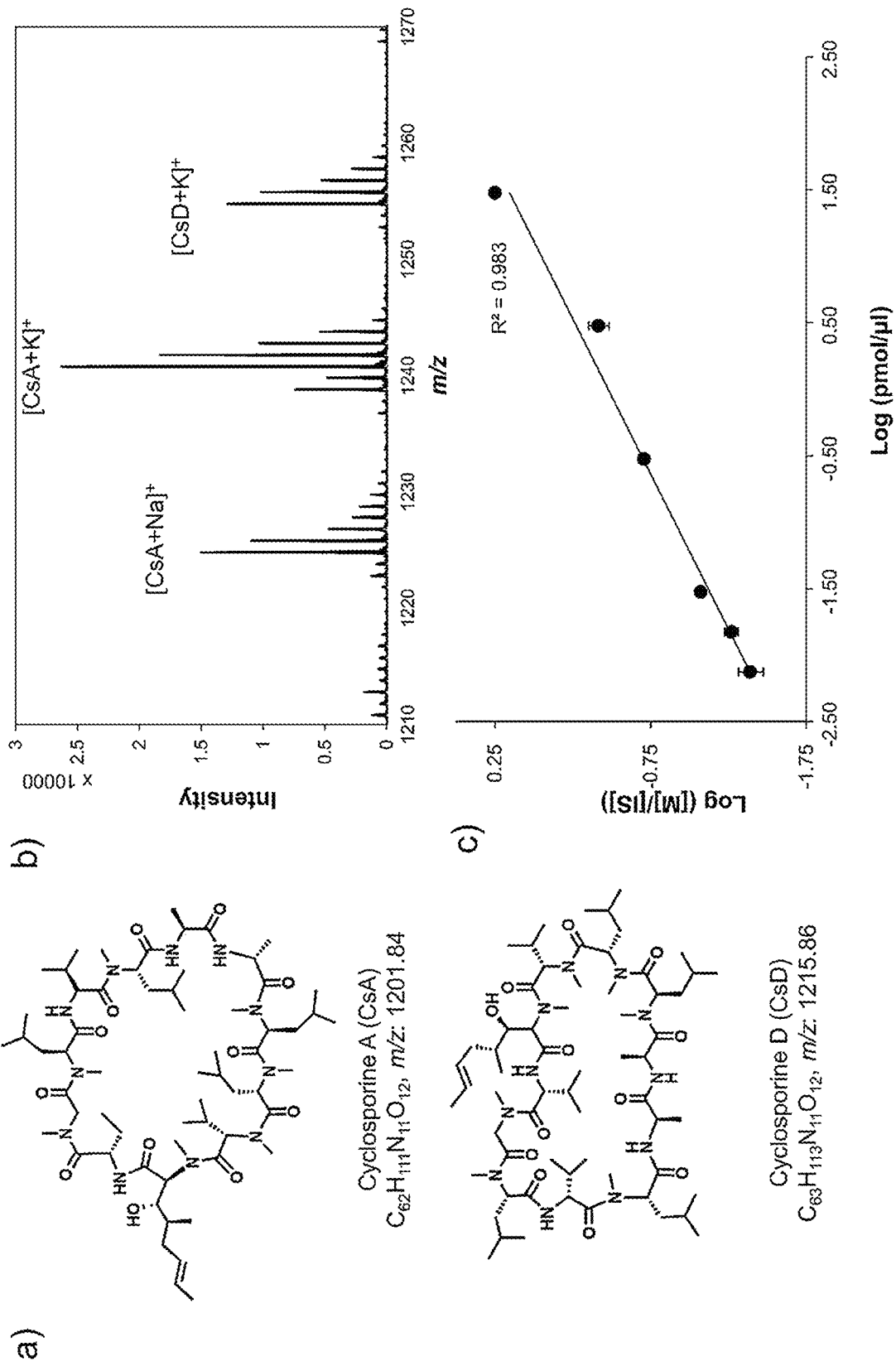
FIG. 4 shows (a) structures of CsA and an internal standard thereof, CsD, (b) an LDI-MS analysis result of CsA (30 pmol/μl) and CsD (30 pmol/μl), and (c) a calibration curve result obtained by LDI-MS analysis from whole blood extracts depending on various concentrations of CsA.

In order to quantify CsA in the blood with Cyclosporine A (CsA) as an immunosuppressive drug, cyclosporine D (CsD) was used as an internal standard similar to CsA as illustrated in FIG. 4. Specifically, 0.5 µl of the whole blood extract to which 30 pmol/µl concentration of CsA was added was spotted on the tungsten disulfide layer of the LDI-MS array of Example 1. And the sample was measured by LDI-MS, and the result is illustrated in FIG. 4.

FIG. 4 shows (a) structures of CsA and an internal standard thereof, CsD, (b) an LDI-MS analysis result of CsA (30 pmol/µl) and CsD (30 pmol/µl), and (c) a calibration curve result obtained by LDI-MS analysis from whole blood extracts depending on various concentrations of CsA.

It can be confirmed from (b) of FIG. 4 that peaks corresponding to the target matter CsA and the internal standard CsD may be clearly distinguished at 1240.81 and 1254.82 m/z. In addition, (c) of FIG. 4 illustrates a constant calibration curve having a coefficient of determination ($R^2$) of 0.983 as a correlation between intensities for a peak corresponding to CsA and a peak corresponding to CsD. The limit of detection (LoD) was measured at 0.0075 pmol/µl, which is much lower than a therapeutic concentration range (0.1 to 0.3 pmol/µl) in whole blood of patients receiving immunosuppressive treatment with CsA.

In addition, it can be seen from these results that the intensity of the peak at 1240.805 m/z corresponding to $[M+K]^+$ of the immunosuppressive drug was affected by the number of spotted layers.

<Quantitative Analysis of TAC>

Figure 5:
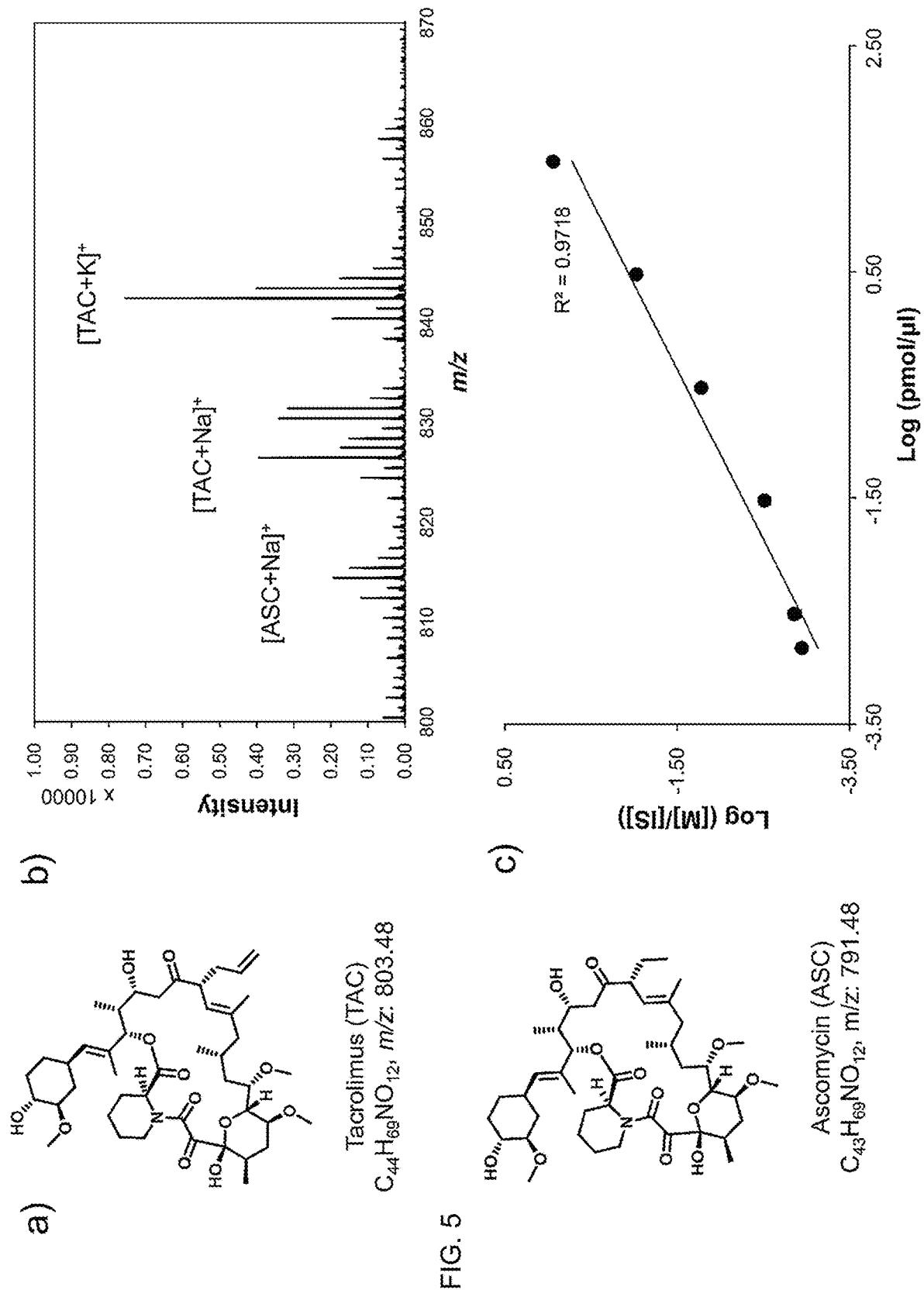
FIG. 5 shows (a) structures of TAC and an internal standard thereof, ASC, (b) an LDI-MS analysis result of TAC (30 pmol/μl) and ASC (30 pmol/μl), and (c) a calibration curve result obtained by LDI-MS analysis from whole blood extracts depending on various concentrations of TAC.

In order to quantify TAC in the blood with Tacrolimus (TAC) as an immunosuppressive drug, ascomycin (ASC) was used as an internal standard similar to TAC as illustrated in FIG. 5, and the quantitative analysis method is the same as that of the quantitative analysis of CsA.

FIG. 5 shows (a) structures of TAC and an internal standard thereof, ASC, (b) an LDI-MS analysis result of TAC (30 pmol/µl) and ASC (30 pmol/µl), and (c) a calibration curve result obtained by LDI-MS analysis from whole blood extracts depending on various concentrations of TAC. TAC and ASC were detected at 842.45 and 830.45 m/z, respectively, corresponding to [M+K]$^+$ for both molecules. The relationship between a normalized peak intensity and a spiked TAC concentration had a linear correlation of 0.97 with the coefficient of determination. It can be seen that the limit of detection was determined to be 0.0015 pmol/μl, which was very sensitive compared to the therapeutic range of 0.006 to 0.025 pmol/μl in the blood of patients treated with TAC. In particular, it can be seen from these results that the problem of not only low ionization properties but also a difficult limit of detection may be significantly alleviated.

<Quantitative Analysis of SIR and EVR>

Figure 6:
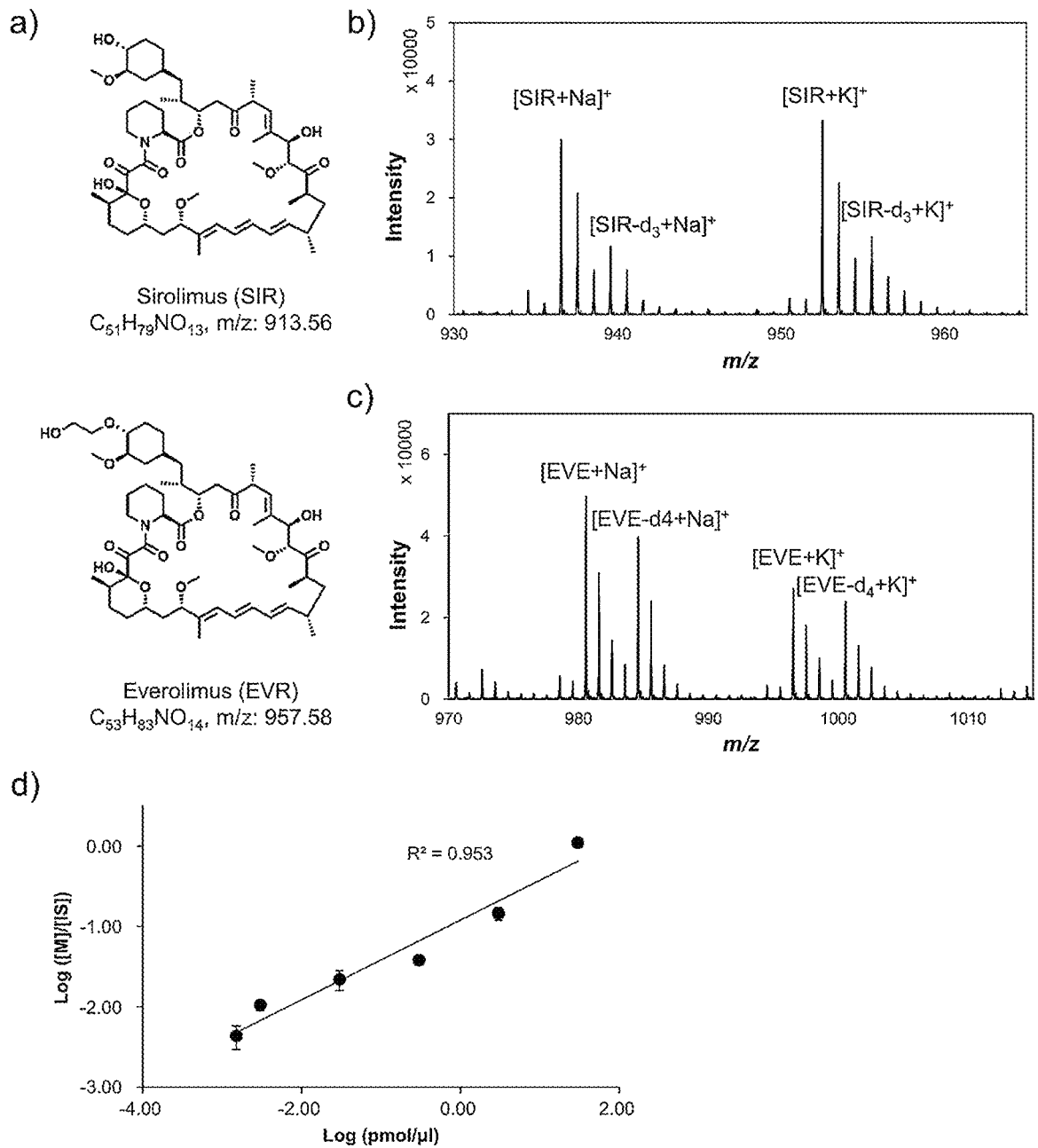
FIG. 6 shows (a) structures of SIR and EVR, (b) an LDI-MS analysis result of SIR (30 pmol/μl) and internal standard (30 pmol/μl), (c) an LDI-MS analysis result of EVR (30 pmol/μl) and internal standard (30 pmol/μl), and (d) a calibration curve result obtained by LDI-MS analysis from whole blood extracts depending on various concentrations of EVR.

In order to quantify Sirolimus (SIR) in the blood with Sirolimus (SIR) and Everolimus (EVR) illustrated in (a) of FIG. 6 as an immunosuppressive drug, respectively, isotope-labeled SIR and EVR were used as internal standards, respectively, and the quantitative analysis method is the same as the quantitative analysis of CsA.

FIG. 6 shows (a) structures of SIR and EVR, (b) an LDI-MS analysis result of SIR (30 pmol/μl) and internal standard (30 pmol/μl), (c) an LDI-MS analysis result of EVR (30 pmol/μl) and internal standard (30 pmol/μl), and (d) a calibration curve result obtained by LDI-MS analysis from whole blood extracts depending on various concentrations of EVR.

As illustrated in FIG. 6, SIR and isotopically labeled SIR-d$_3$ were detected at 936.56 and 939.57 m/z corresponding to [M+Na]$^+$, respectively, and calibration curves were obtained by analysis of SIR with an internal standard in the concentration range of 0015 to 30 pmol/μl. The limit of detection was determined to be 0.0015 pmol/μl, which is much lower than the therapeutic range of 0.005 to 0.011 pmol/μl for whole blood.

For EVR, its internal standard was detected at 980.57 and 984.59 m/z corresponding to [M+Na]$^+$. The limit of detection was determined to be 0.0015 pmol/μl, sensitive enough to quantify EVR in the whole blood of patients.

Figure 7:
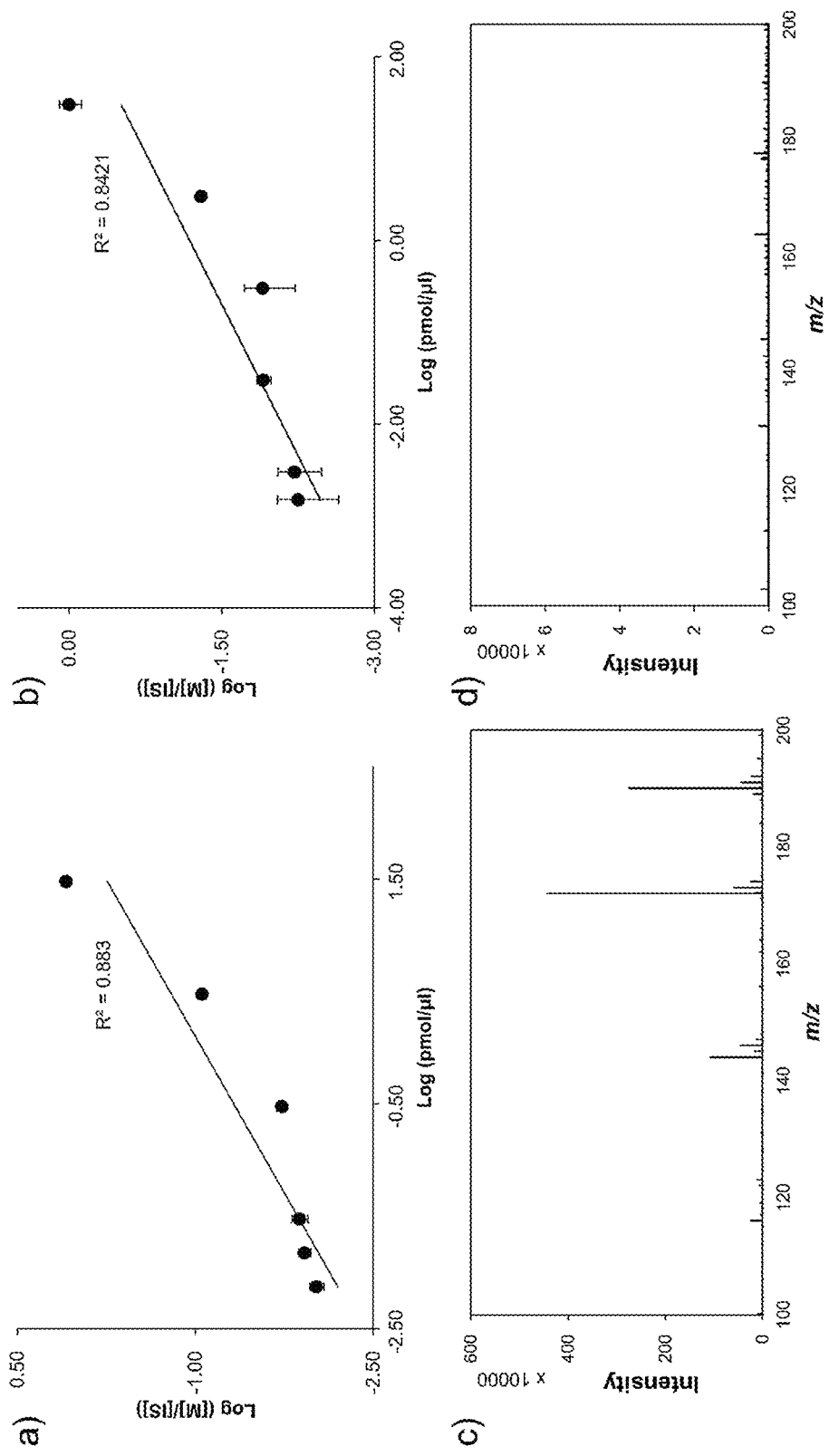
FIG. 7 shows (a) a measurement result for a quantitative range (0.0075 to 30 pmol/μl) of CsA using an α-cyano-4-hydroxycinnamic acid (CHCA) matrix for ionization, (b) a measurement result for a linear quantitative range for TAC (0.0015 to 30 pmol/μl) using the matrix, (c) a low molecular weight region MALDI-MS spectrum of a CHCA-treated sample, and (d) a low mass region LDI-MS spectrum according to the present invention.

MADLI-MS is a universal method for detecting drugs and metabolites in biological samples, which is advantageous for rapid analysis, but has a problem of matrix interference. As illustrated in FIG. 7, analysis using α-cyano-4-hydroxycinnamic acid (CHCA) as a matrix for detecting CsA in a blood sample found multiple peaks around 190.09, 172.07 and 212.06 m/z corresponding to CHCA itself and fragments thereof ([M]$^+$, [M−OH]$^+$ and [M+Na]$^+$).

That is, MADLI-MS can confirm the degree of fragmentation pattern of molecules through analysis, but is difficult to analyze precisely because of the presence of various peaks due to the matrix. In addition, the conventional MADLI-MS, which requires crystallization with an analyte using the matrix, is particularly difficult to reproduce and quantify because sweet spots and silent spots are formed.

FIG. 7 shows (a) a measurement result for a quantitative range (0.0075 to 30 pmol/μl) of CsA using an α-cyano-4-hydroxycinnamic acid (CHCA) matrix for ionization, (b) a measurement result for a linear quantitative range for TAC (0.0015 to 30 pmol/μl) using the matrix, (c) a low molecular weight region MALDI-MS spectrum of a CHCA-treated sample, and (d) a low mass region LDI-MS spectrum according to the present invention.

In (a) and (b) of FIG. 7, MALDI-MS analysis results of CsA and TAC using CHCA showed poor calibration curves with low R$_2$ values (0.88 and 0.84, respectively). In addition, the analysis results of TAC showed 60% of the coefficient of variation due to variation within the sample. From these results, it can be confirmed that the LDI-MS platform according to the present invention exhibits improved performance enabling higher sensitivity compared to the MALDI-MS technology. In addition, in the analysis of CsA and TAC using the CHCA matrix, the limits of detection were determined to be 0.015 and 0.03 pmol/μl, respectively. Therefore, it can be seen that the measurement of organic matter in the blood using LDI-MS according to the present invention includes easy experimentation and analysis, and is sensitive and excellent in reproducibility compared to the analysis method using a matrix.

Figure 8:
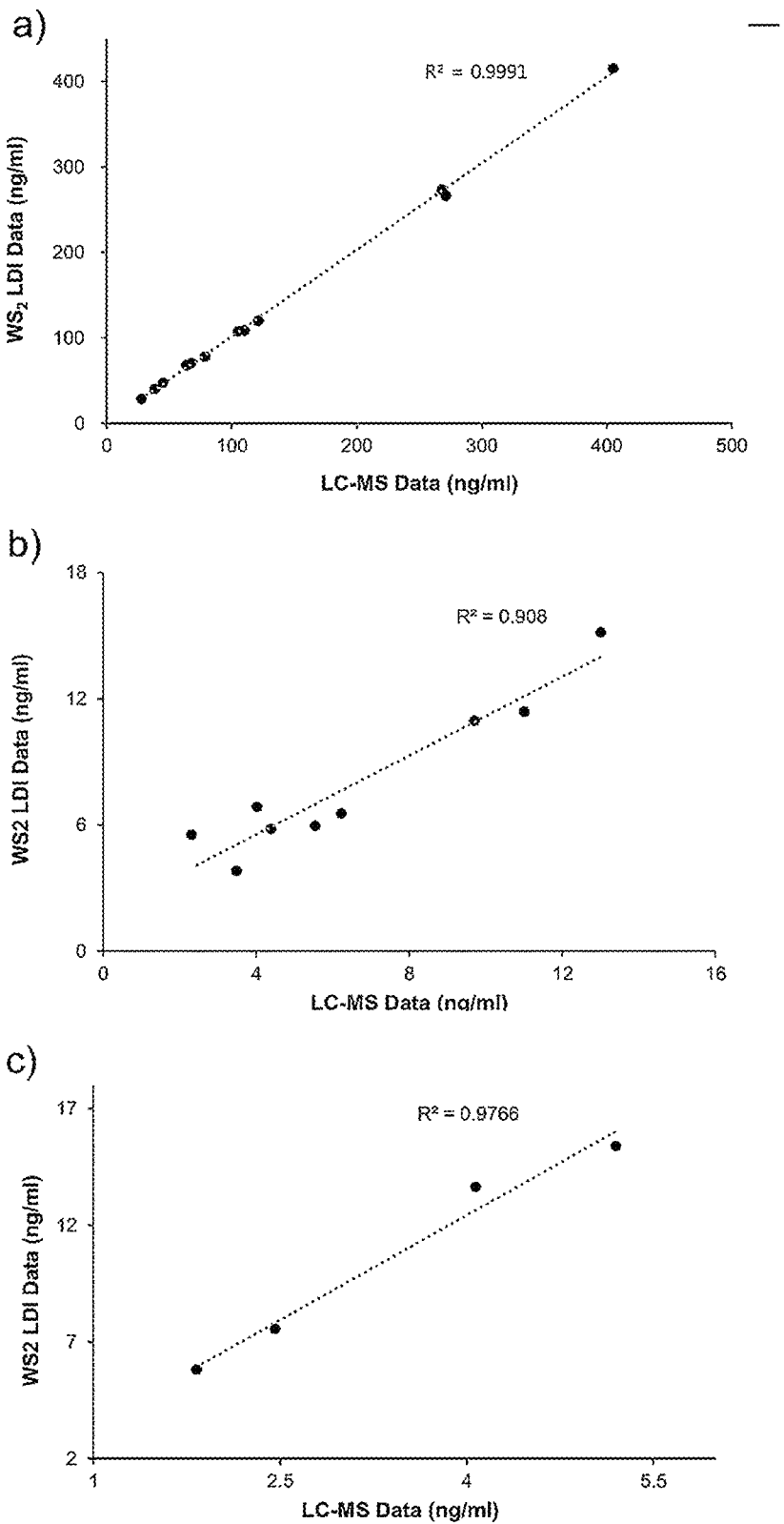
FIG. 8 illustrates the correlation between LDI-MS of Experimental Example 3 and conventional LC-MS, and is data obtained by comparing and analyzing quantitative results of three types of immunosuppressive drugs, CsA (a), TAC (b) and EVR (c) by WS$_2$-based LDI-MS analysis (y-axis) and HPLC-ESI-MS/MS (x-axis).

[Experimental Example 4] Comparative Evaluation with Conventional LC-MS for Quantitative Analysis of Immunosuppressive Drug FIG. 8 illustrates the correlation between LDI-MS of Experimental Example 3 and conventional LC-MS, and is data obtained by comparing and analyzing quantitative results of three types of immunosuppressive drugs, CsA (a), TAC (b) and EVR (c) by WS$_2$-based LDI-MS analysis (y-axis) and HPLC-ESI-MS/MS (x-axis). Specifically, it was possible to quantify organic matter in the blood through LDI-MS analysis based on absolute quantification of therapeutic drugs using internal standards. The LDI-MS result (a) quantifying CsA in the blood injected with CsA showed an excellent correlation with the LC-MS result, and the TAC case (b) and the EVR case (c) also allowed quantification of therapeutic drugs having acceptable correlations even at the required LoD and therapeutic concentrations.

Figure 9:
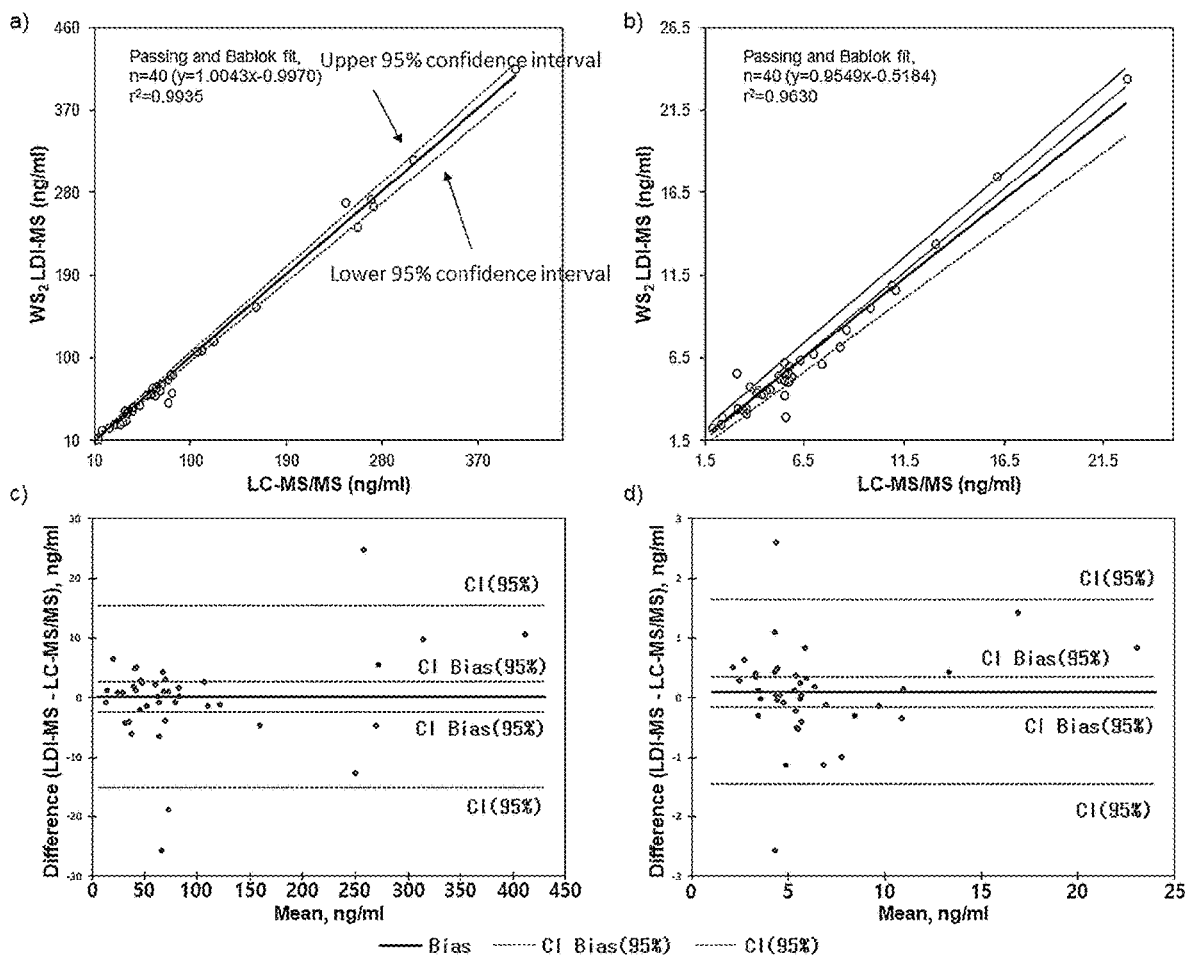
FIG. 9 shows Passing-Bablok regression analyzes data for measurement values analyzed by WS$_2$ LDI-MS and measurement values analyzed by LC-MS/MS for a total of 80 samples of blood patients injected with CsA and TAC. Specifically, (a) of FIG. 9 is Passing-Bablok regression analyses (dashed lines represent 95% confidence intervals) data for comparative measurements of WS$_2$ LDI-MS and LC-MS/MS of the samples of blood patients injected with CsA, and (b) of FIG. 9 is Passing-Bablok regression analyses (dashed lines represent 95% confidence intervals) data for comparative measurements of WS$_2$ LDI-MS and LC-MS/MS of the samples of blood patients injected with TAC. Also, (c) of FIG. 9 is Bland-Altman plots data of comparative measurements of WS$_2$ LDI-MS and LC-MS/MS of the samples of blood patients injected with CsA, and (d) of FIG. 9 is Bland-Altman plots data of comparative measurements of WS$_2$ LDI-MS and LC-MS/MS of the samples of blood patients injected with TAC.

In addition, after comparing the measured values analyzed by WS$_2$ LDI-MS and LC-MS/MS of the method of Experimental Example 3 for a total of 80 samples of blood patients, including 40 samples of blood patients injected with Cyclosporine A (CsA) and 40 samples of blood patients injected with Tacrolimus (TAC), the agreement between the two measured values was evaluated through the Passing-Bablok regression and the Bland-Altman plot, and the evaluation results are shown in FIG. 9.

Passing-Bablok regression is a linear regression method that calculates the slope and intercept values of a straight line corresponding to a 95% confidence interval from the correlation plots of two data sets. It can be determined that the measured values of the two data sets match if 1 and 0 are included between the slope and intercept values of a lower 95% confidence interval line and an upper 95% confidence interval line, respectively.

FIG. 9 illustrates Passing-Bablok regression analyzes data for measurement values analyzed by WS$_2$ LDI-MS and measurement values analyzed by LC-MS/MS for a total of 80 samples of blood patients injected with CsA and TAC. Specifically, (a) of FIG. 9 is Passing-Bablok regression analyses (dashed lines represent 95% confidence intervals) data for comparative measurements of WS$_2$ LDI-MS and LC-MS/MS of the samples of blood patients injected with CsA, and (b) of FIG. 9 is Passing-Bablok regression analyses (dashed lines represent 95% confidence intervals) data for comparative measurements of WS$_2$ LDI-MS and LC-MS/MS of the samples of blood patients injected with TAC. Also, (c) of FIG. 9 is Bland-Altman plots data of comparative measurements of WS$_2$ LDI-MS and LC-MS/MS of the samples of blood patients injected with CsA, and (d) of FIG. 9 is Bland-Altman plots data of comparative measurements of WS$_2$ LDI-MS and LC-MS/MS of the samples of blood patients injected with TAC.

In FIG. 9, in the case of the CsA analysis result (a), the slopes of the lower 95% confidence interval line and the upper 95% confidence interval line are 0.9666 and 1.0317, respectively, so 1 is included in this range. In addition, the intercept values of the lower 95% confidence interval line and the upper 95% confidence interval line are −1.1676 and 2.9968, respectively, so 0 is included in this range. In addition, in the case of the TAC analysis result (b), the same result was shown. The Bland-Altman plot is also a technique for evaluating the agreement between two measurements, and if 0 is included in the 95% confidence interval bias value, the two measurements are considered to be consistent. In the case of CsA data analysis result (c), the 95% confidence interval bias values are −2.356 and 2.628 (blue dotted line), and 0 is included between these values, indicating that the $WS_2$ LDI-MS and LC-MS/MS measurement results are consistent with each other. In addition, in the case of the TAC analysis result (d), the same result was shown. Therefore, it can be seen that the measured values obtained through $WS_2$ LDI-MS are statistically consistent with the LC-MS/MS measured values.

It can be seen from these results that the $WS_2$ LDI-MS measurement method according to the present invention is a platform of which an analysis and a preparing process are simply compared to LC-MS/MS, is very efficient in terms of cost and time, has an advantage that a quantitative analysis may be performed immediately and in real time, has an effect that qualitative and quantitative analyses may be performed with the same precision as or higher precision than LC-MS/MS, and may substitute for LC-MS/MS that is complicated and low efficiency through high efficiency and economical efficiency

The invention claimed is:

1. A method for analyzing a sample in blood using LDI-MS, comprising:
    a sample loading step of loading the sample containing the blood on a tungsten disulfide layer of an LDI-MS sample loading array including a substrate layer and the tungsten disulfide layer stacked on the substrate layer; and
    an analyzing step of analyzing the sample loaded on the LDI-MS sample loading array by LDI-MS to detect a target matter in the sample.

2. The method for analyzing a sample in blood using LDI-MS of claim 1, wherein the tungsten disulfide layer includes a plurality of tungsten disulfide nanoflake particles in contact with the substrate layer.

3. The method for analyzing a sample in blood using LDI-MS of claim 1, wherein the analyzing step includes a quantifying step of calculating a content of the target matter.

4. The method for analyzing a sample in blood using LDI-MS of claim 3, wherein the quantifying step includes a first quantifying step of obtaining a concentration of tungsten disulfide nanoflake particles present in the tungsten disulfide layer, and
    the content of the target matter is determined from the concentration of the tungsten disulfide nanoflake particles obtained in the first quantifying step.

5. The method for analyzing a sample in blood using LDI-MS of claim 3, further comprising, before the sample loading step, adding an internal standard to a liquid sample,
    wherein the quantifying step includes a second quantifying step of determining the content of the target matter from a peak intensity corresponding to the target matter and a peak intensity corresponding to the internal standard in an LDI-MS spectrum.

6. The method for analyzing a sample in blood using LDI-MS of claim 5, wherein the quantifying step includes obtaining a correction spectrum, and a coefficient of determination in the correction spectrum is 0.9 or more.

7. The method for analyzing a sample in blood using LDI-MS of claim 1, wherein a limit of detection (LoD) is 0.01 pmol/μl (target matter/blood) or less.

8. An LDI-MS sample loading array for detecting an organic matter in blood, comprising:
    a substrate layer; and
    a tungsten disulfide layer stacked on the substrate layer and allowing a sample containing the blood to be loaded.

9. The LDI-MS sample loading array for detecting an organic matter in blood of claim 8, wherein the tungsten disulfide layer includes a plurality of tungsten disulfide nanoflake particles in contact with the substrate layer.

10. The LDI-MS sample loading array for detecting an organic matter in blood of claim 9, wherein the tungsten disulfide nanoflake particles have an average thickness of 2 to 15 nm.

11. The LDI-MS sample loading array for detecting an organic matter in blood of claim 9, wherein the tungsten disulfide nanoflake particles are present in an amount of 0.0001 to 100 mg/cm² per unit area.

12. The LDI-MS sample loading array for detecting an organic matter in blood of claim 9, wherein the tungsten disulfide layer is prepared by spotting an aqueous dispersion solution in which the tungsten disulfide nanoflake particles are dispersed, on the substrate layer, and then evaporating water.

13. The LDI-MS sample loading array for detecting an organic matter in blood of claim 12, wherein the aqueous dispersion solution contains 0.001 to 10% by weight of the tungsten disulfide nanoflake particles.

14. The LDI-MS sample loading array for detecting an organic matter in blood of claim 13, wherein the aqueous dispersion solution is spotted twice or more in the same area in a content of 0.001 to 100 μl (25° C. and 1 atm).

15. The LDI-MS sample loading array for detecting an organic matter in blood of claim 9, wherein the tungsten disulfide nanoflake particles satisfy Equation 1:

$$R_1/R_2 \geq 1.3$$

wherein $R_1$ is a peak area in a range of 340 to 380 cm$^{-1}$ in a Raman spectrum measured in an arbitrarily selected region of 2×2 μm in the tungsten disulfide layer, and $R_2$ is a peak area in a range of 400 to 440 cm$^{-1}$ in the Raman spectrum.

16. The LDI-MS sample loading array for detecting an organic matter in blood of claim 9, wherein the tungsten disulfide nanoflake particles are prepared by a lithium-intercalated chemical exfoliation method from tungsten disulfide bulk powders.

17. The LDI-MS sample loading array for detecting an organic matter in blood of claim 8, wherein the tungsten disulfide layer has an average thickness of 0.001 to 500 μm.

18. The LDI-MS sample loading array for detecting an organic matter in blood of claim 8, wherein the substrate layer includes any one or two or more selected from aluminum, copper, iron, nickel, zinc, chromium, silver, and silicone.

* * * * *